United States Patent
Ettner et al.

(10) Patent No.: US 6,773,703 B1
(45) Date of Patent: Aug. 10, 2004

(54) PROTEIN-CONTAINING HYDROGELS

(75) Inventors: Norbert Ettner, Aichach (DE); Michael Schink, Hamburg (DE); Jörg Schreiber, Hamburg (DE); Wolfgang Meier, Basel (CH); Marc Sauer, Celle (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/493,887

(22) Filed: Jan. 28, 2000

(30) Foreign Application Priority Data

Jan. 29, 1999 (DE) .......................... 199 03 655

(51) Int. Cl.⁷ .......................... A61K 38/43; A61K 9/00; A61F 13/00; A61F 2/00
(52) U.S. Cl. ..................... 424/94.1; 424/400; 424/422; 424/423
(58) Field of Search ............... 424/400, 94.1, 424/422, 423, 419, 445, 443

(56) References Cited

U.S. PATENT DOCUMENTS

| | | | |
|---|---|---|---|
| 5,000,955 A | 3/1991 | Gould et al. | 424/409 |
| 5,733,563 A | 3/1998 | Fortier | 424/422 |
| 5,804,213 A | 9/1998 | Rolf | 424/445 |

FOREIGN PATENT DOCUMENTS

| | | |
|---|---|---|
| WO | 96/31551 | 10/1996 |
| WO | 96/39125 | 12/1996 |
| WO | 98/22153 | 5/1998 |

OTHER PUBLICATIONS

Galin et al., Makromol. Chem., 175(3), 991–1000, 1974, abstract.*
"Collangenase Therapy in the Treatment of Decubitus Ulcers" (Nano, et al., 1996, in: Proteolysis in Wound Repair, Abatangelo, Donati and Vanscheidt (Eds.), Springer Verlag, Berlin, p. 61).
"Enzymatic Debridement of Burn Wounds" (J. Hansbrough & W. Hansbrough, 1996, in: Proteolysis in Wound Repair, Abatangelo, Donati und Vanscheidt (Eds.), Springer Verlag, Berlin, p. 97).

* cited by examiner

Primary Examiner—Maryam Monshipouri
(74) Attorney, Agent, or Firm—Norris McLaughlin & Marcus PA

(57) ABSTRACT

Hydrogel comprising at least one protein and/or enzyme and/or SOD/catalase enzyme mimic and PEGs, and parts of proteins and enzymes and/or recombinant proteins and enzymes, the proteins and/or enzymes being connected to the PEGs via urea groups.

18 Claims, 2 Drawing Sheets

PROTEIN-CONTAINING HYDROGELS

Figure 1:
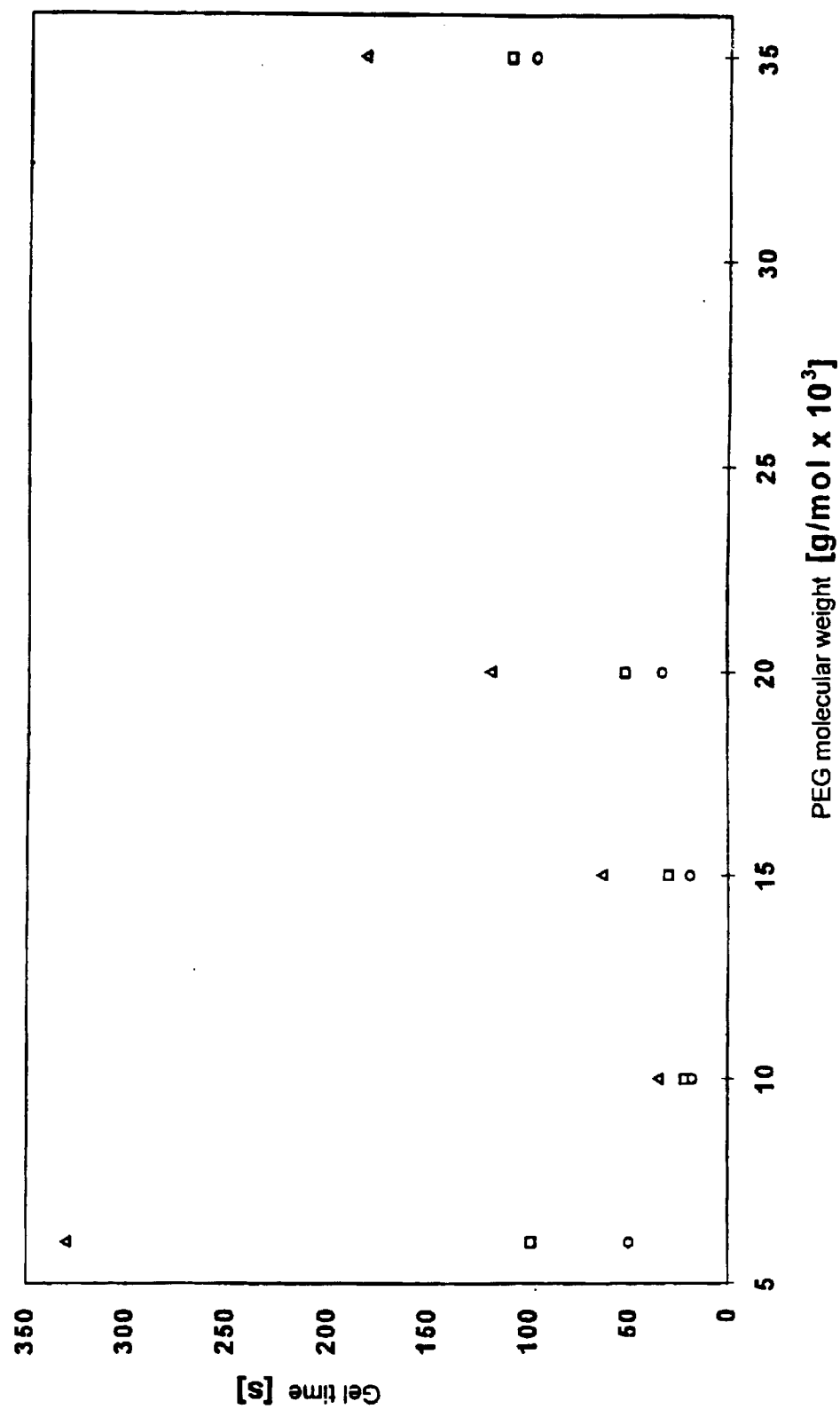

The healing of therapy-resistant wounds has since time immemorial been a great challenge to medicine and science. Present-day specifications for the function of interactive dressings for chronic wounds derive from Winter (1962, Nature 193, 293) and have recently been reformulated by Turner (1994, Wound Rep. Reg. 2, 202). The emphasis in this connection is on the creation of a moist wound healing environment which, in contrast to traditional dry wound treatment with, for example, gauze compresses, provides physiological and thus better conditions for the natural processes of wound healing.

The principle of moist wound healing can at present be regarded as the state of the art in the therapy of wounds which are healing with difficulty or not at all. The dressing must absorb most of the exudate but, at the same time, leave on the wound itself a liquid film in which the actual moist wound healing takes place. Dry wounds and those with little exudation must be provided with adequate moisture to achieve rehydration of the dehydrated tissue. In the moist wounds which have been established in this way there is then proliferation of new blood vessels and reduced bacterial growth, with a suitable pH being set up. These requirements are met by sponge-like structures such as, for example, hydrogels which have an excess in the form of bound water.

Hydrogels are generally produced by hydrophilic, coherent monomers forming in a dispersant a three-dimensional network structure into whose interstices the dispersant, normally water, can infiltrate. A hydrogel should have a certain oxygen permeability and assume a barrier function towards microbes possibly penetrating in from the environment. Fundamental requirements for a hydrogel are also a simple production process and a certain storage stability.

The use and the variety of possible uses of hydrogels in wound treatment, and their composition and production are sufficiently well documented (Peppas in: Hydrogels in Medicine and Pharmacy, 1986, CRC Press, Volume II, Chapter 4). Hydrogels are preferably employed for treating dry necrotic wounds such as, for example, burns and chronic venous ulcers (Thomas, in: Wound Management and Dressings, 1990, The Pharmaceutical Press, London, p. 50).

They are made of insoluble polymeric materials able to swell in aqueous media. They should furthermore have a high water content, be inert to biological processes, permeable for cellular metabolites and, in particular, not induce any irritation on contact with living tissue.

A bioartificial or semisynthetic hydrogel can be synthesized by covalently linking the hydrophilic synthetic monomer to the surface of a protein, whereupon there is formation of a three-dimensional polymer-protein matrix inside the dispersant. This class of hydrogels made from synthetic polymers and biopolymers have recently become the subject of research, These novel biomaterials are referred to as bioartificial hydrogels (Giusti et al., 1993, Trends in Polymeric Science, 9, 261).

U.S. Pat. No. 5,804,213 reports on the production of a biologically active, water-containing gel as wound dressing. In this case, a dry, hydrocolloidal polymer is mixed with water and a biologically active substance.

The use of dehydrated, crosslinked collagen materials as drug delivery system is described in WO 98/22153. In WO 96/31551, proteins or peptides in the dry state are mixed as active agents with polyurethane-crosslinked microgels. The microgels swell in an aqueous medium to give hydrogels and release the protein or peptide again from the hydrogel matrix. Moreover U.S. Pat. No. 5,000,955 describes polyurethane hydrogels for cosmetic, biological and medical applications.

Cubic phases made of glyceryl monooleate are able to immobilize enzymes by non-covalent linkages, as reported in WO 96/39125. In this case, the enzymatic activity is retained due to the immobilization and is even increased over a lengthy period by comparison with dissolved enzyme. It should furthermore be emphasized that the barrier function of the gel matrix suppresses the proteolytic degradation of the immobilized enzymes occurring in the wound fluid.

Hydrogels of particular interest are those in which a biomolecule is covalently incorporated, as described in U.S. Pat. No. 5,733,563 and in 1994 by Fortier (1994, Biotechnol.Techn., 8, 71). These hydrogels are formed by copolymerization of a polyethylene glycol which has been activated by 4-nitrophenyl chloroformate and of bovine serum albumin in borate buffer. In this case, the activated group may react with an amino, SH—, OH— or COOH group in the protein.

Disadvantages of the bioartificial hydrogels known in the state of the art are the long gel times of from 20 up to 270 minutes, the formation of cleavage products in the form of p-nitrophenols in the hydrogel matrix and the impossibility of crosslinking oligomeric proteins such as, for example dimeric SOD or tetrameric catalase stably with the polyethylene glycol which has been activated with 4-nitrophenyl chloroformate.

It is an object of the invention to make water-insoluble, water-swellable hydrogels which have short gel times, can be employed for medical purposes and are particularly suitable for promoting the healing of chronic wounds.

This object is achieved by a hydrogel which comprises at least one protein and/or enzyme and PEGs, the proteins and/or enzymes being connected to the PEGs via urea groups.

In the production of the hydrogel there is use of additional substances which interact with the oxygen species (ROS) present in wound fluids of chronic wounds, that is to say with factors which impede the wound healing process, these additional substances being covalently polymerized into the hydrogel. The invention describes the novel production of protein-containing hydrogels with which it is possible to render ROS in the wound fluid of chronic wounds harmless. It describes the production of collagenase-containing and trypsin-containing hydrogels for treating necrotic deposits covering wounds, and the production of lysozyme-containing hydrogels which can be employed for controlling bacteria which have infected wounds. The feasibility of incorporating biologically active substances such as, for example, antibiotics, growth factors and other active ingredients into the hydrogels is also described.

The present invention makes use of the reaction of, in particular, $\alpha,\omega$-diisocyanato-polyethylene glycols with protein to form a protein-containing hydrogel in an aqueous medium. In this case, the crosslinking reaction of the isocyanate with the amino groups of the protein is a reaction which is preferred owing to the higher nucleophilicity by comparison with hydrolysis of the isocyanate to the amine with formation of carbon dioxide. The reaction represents one possibility for the three-dimensional crosslinking of polyethylene glycol and proteins without the occurrence of cleavage products resulting from the activated group. It is furthermore possible to form stable hydrogels with oligomeric proteins such as, for example, SOD and catalase.

Polyethylene glycols (PEGs) belong to the class of polyalkylene glycols which are polyethers of the general formula (Römpp Lexikon Chemie—Version 1.3, Stuttgart/ New York: Georg Thieme Verlag 1997):

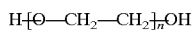

Polyethylene glycols (PEGS) are produced industrially by base-catalysed polyaddition of ethylene oxide (oxirane) in systems which usually contain small amounts of water with ethylene glycol as starter molecule. They have molecular weights in the range of about 200–5 000 000 g/mol, corresponding to degrees of polymerization n of about 5 to >100 000. In the wider sense, products with n=2–4 (di-, tri- and tetraethylene glycol) are also included in the PEGs; they can be produced mol. uniformly, whereas the PEGs with higher molecular weights are polymol, that is to say consist of populations of macromolecules with different molecular weights.

Liquid products with molecular weights <about 25 000 g/mol are referred to as proper polyethylene glycols, while the solid ones of higher molecular weight (melting point about 65° C.) are referred to as polyethylene oxides. Polyethylene oxides have an extremely low concentration of reactive hydroxyl end groups and show only weak glycol properties.

Branched polyadducts of ethylene glycol and polyhydric alcohols are also referred to as PEG.

PEG are liquid or waxy to solid products which are readily soluble in water up to about 100° C. and many organic solvents. Aqueous solutions have noticeable rheological properties; thus, some solutions show pronounced viscoelasticity. Even tiny amounts of PEG cause the so-called Toms effect (a reduction in frictional resistance) in flowing water. PEG products are very stable to hydrolysis but sensitive to oxidation at elevated temperatures. Their chemical reactivity is determined by the terminal hydroxyl groups, which are easily esterified (to give polyethylene glycol esters) or etherified (to give polyalkylene glycol ethers) or can be reacted with isocyanates to give urethanes.

PEG are categorized as toxicologically acceptable. Their biodegradability is very dependent on the molecular weight; products with low molecular weights, for example 4000 g/mol, are up to 80% degraded.

PEGs are used inter alia as solubilizers, binders, thickeners, emulsifiers, dispersants, protective colloids, plasticizers or release agents for a wide variety of applications; as binders for ceramic compositions, sizes, flocculants, adhesive components, to reduce the resistance to flow of aqueous liquids (drag reduction), as intermediates for polymer syntheses, for example on a large scale for producing polyurethanes; high molecular weight PEGs as starch substitute and for producing films and sheets.

The PEG employed advantageously has a molecular weight of from 8,000 to 18,000 g/mol, in particular 10,000 to 15,000 g/mol.

It is also possible according to the invention to employ modified PEGs, which may have the following structural schemes:

A—B—A (1)

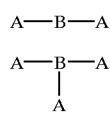

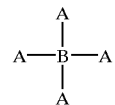

where B symbolizes a hydrophilic region in the particular crosslinker molecule, and A represents an isocyanate group, and which may differ in chemical nature within one molecule.

Likewise within the scope of the invention submitted herewith are structural schemes as follows:

A—B—Z—B—A (9)

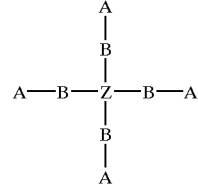

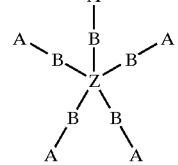

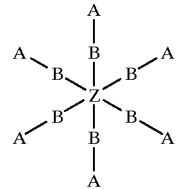

where Z in this case represents a central unit which may be hydrophilic or hydrophobic and usually comprises an oligo- or polyfunctional molecular residue.

Linker substances with a higher degree of branching of course also fall within the scope of the present invention.

For example, Z in the scheme (10) may comprise a glyceryl radical whose three OH functionalities pass over into the B regions which in turn may represent, for example, polyoxyethylene chains of equal or unequal length, and whose terminal OH group is esterified with a long chain fatty acid. Partial substitution on the glycerol is also conceivable and may result in structures corresponding to scheme (9).

Possible examples of more specific structural schemes for structural scheme (1) are as follows:

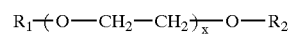

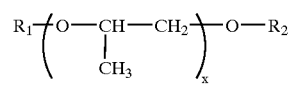

-continued

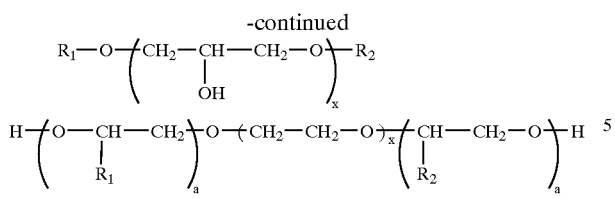

where $R_1$, $R_2$, $R_3$, R4, $R_5$ and $R_6$ represent, independently of one another, isocyanate groups or branched or unbranched, saturated or unsaturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylated or arylated organylsilyl radicals, but where at least one of these radicals represents an isocyanate group. In this connection, x, y and z denote, independently of one another, numbers which allow the complete molecule to be soluble or at least dispersible in water, typically selected from the range above 10, advantageously from the range from 20 to $10^7$, a and b are numbers which are selected depending on x so that the linker substance has an at least adequate stability in water or dispersibility in water. It is possible in individual cases, for example when the thickener is chosen from the group of derivatized polysaccharides, for x to assume where appropriate considerably higher values than, for example, 300, even several millions. This is known per se to the skilled person and requires no further explanation.

Possible examples of more specific structural schemes for structural scheme (2) are as follows:

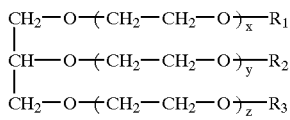

where $R_1$, $R_2$ and $R_3$ may represent, independently of one another, isocyanate groups or branched or unbranched, unsaturated or saturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylated or arylated organylsilyl radicals, but where at least one of these radicals represents an isocyanate group. In this case, x, y and z denote, independently of one another, numbers which permit the complete molecule to be soluble or at least dispersible in water, typically chosen from the range above 10, advantageously from the range from 20 to $10^7$.

Partial substitution is also conceivable in this connection, in which case one or more of the indices x, y or z may assume the value zero, and one or more of the radicals $R_1$, $R_2$ or $R_3$ may represent hydrogen atoms.

Possible examples of more specific structural schemes for the structural scheme (3) are as follows:

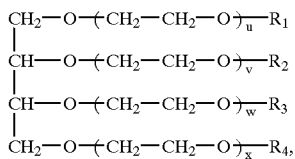

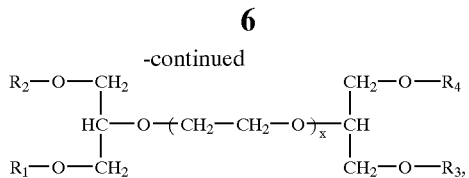

where $R_1$, $R_2$, $R_3$ and R4 may represent, independently of one another, isocyanate groups or branched or unbranched, saturated or unsaturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylated or arylated organylsilyl radicals, but where at least one of these radicals represents an isocyanate group. In this case, x, y and z denote, independently of one another, numbers which permit the complete molecule to be soluble or at least dispersible in water, typically chosen from the range above 10, advantageously from the range from 20 to $10^7$.

It is also, of course, true in this case that partial substitution is conceivable, in which case one or more of the indices u, v, w, x may assume the value zero, and one or more of the radicals $R_1$, $R_2$, $R_3$ or R4 may represent hydrogen atoms. In this case, these substances naturally pass over into other structural schemes.

Possible examples of more specific structural schemes for structural scheme (9) are as follows:

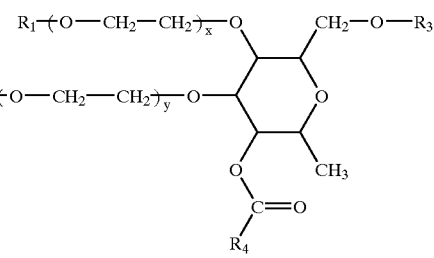

where $R_1$, $R_2$, $R_3$ and R4 may represent, independently of one another, isocyanate groups or branched or unbranched, unsaturated or saturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylate or arylated organylsilyl radicals, but where at least one of these radicals represents an isocyanate group. In this case, x, y and z denote, Independently of one another, numbers which permit the complete molecule to be soluble or at least dispersible in water, typically chosen from the range above 10, advantageously from the range from 20 to $10^7$.

Possible examples of more specific structural schemes for the structural scheme (10) are as follows:

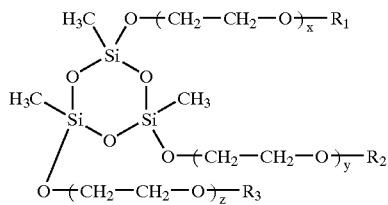

-continued

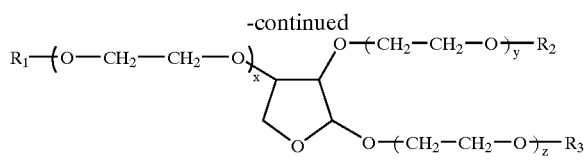

where $R_1$, $R_2$, and $R_3$ may represent, independently of one another, isocyanate groups or branched or unbranched, saturated or unsaturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylated or arylated organylsilyl radicals, but where at least one of these radicals represents an isocyanate group. In this case, x, y and z denote, independently of one another, numbers which permit the complete molecule to be soluble or at least dispersible in water, typically chosen from the range above 10, advantageously from the range from 20 to $10^7$.

A possible example of a more specific structural scheme for structural scheme (11) is as follows:

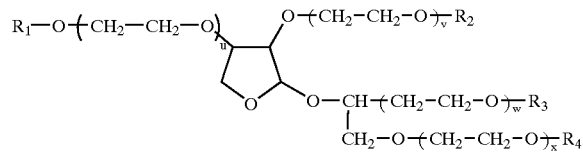

where $R_1$, $R_2$, $R_3$ and R4 may represent, independently of one another, isocyanate groups or branched or unbranched, saturated or unsaturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylated or arylated organylsilyl radicals, but where at least one of these radicals represents an isocyanate group. In this case, x, y and z denote, independently of one another, numbers which permit the complete molecule to be soluble or at least dispersible in water, typically chosen from the range above 10, advantageously from the range from 20 to $10^7$.

A possible example of a more specific structural scheme for structural scheme (12) is as follows:

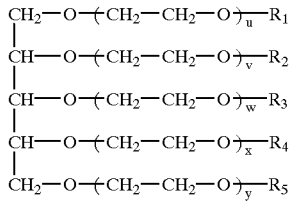

where $R_1$, $R_2$, $R_3$, R4 and $R_5$ may represent, independently of one another, isocyanate groups or branched or unbranched, saturated or unsaturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylated or arylated organylsilyl radicals, but where at least one of these radicals represents an isocyanate group. In this case, x, y and z denote, independently of one another, numbers which permit the complete molecule to be soluble or at least dispersible in water, typically chosen from the range above 10, advantageously from the range from 20 to $10^7$.

A possible example of a more specific structural scheme for structural scheme (13) is as follows:

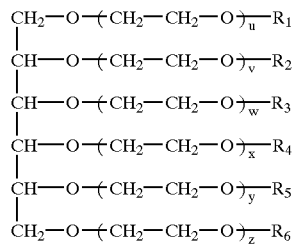

where $R_1$, $R_2$, $R_3$, R4, $R_5$ and $R_6$ may represent, independently of one another, isocyanate groups or branched or unbranched, saturated or unsaturated, cyclic or chain-like aliphatic, aromatic or heteroaromatic radicals, for example branched or unbranched or cyclic alkyl or alkanoyl radicals, or aryl or aroyl radicals which are unsubstituted or substituted by alkyl or aryl substituents, or else alkylated or arylated organylsilyl radicals, but where at least one of these radicals represents an isocyanate group. In this case, x, y and z denote, independently of one another, numbers which permit the complete molecule to be soluble or at least dispersible in water, typically chosen from the range above 10, advantageously from the range from 20 to $10^7$.

It is also advantageous where appropriate for the structural schemes described above to be modified so that renewed branching occurs at the end of the thickener molecule, for example in the way implemented in the group of so-called dendrimers.

The choice of the protein necessary to produce the hydrogel depends on the required properties of the hydrogel. Suitable in principle are all proteins and enzymes, and parts of proteins and enzymes or recombinant proteins and enzymes such as, for example:

antibodies free-radical detoxifying enzymes such as, for example, superoxide dismutase, catalase, glutathione peroxidase, myeloperoxidase and/or combinations thereof, and SOD/catalase enzyme mimics enzymes with proteolytic activity, such as collagenase, trypsin, elastase and/or combinations thereof protease inhibitors from the class of tissue inhibitors of matrix metalloproteinases (TIMPs) and/or other proteinogenic protease inhibitors such as aprotinin, soya bean trypsin inhibitor and alpha-2 macroglobulin enzymes with antimicrobial activity, such as, for example, lysozyme and hydrolase enzymes with phosphorylating activity, such as phosphatases and kinases growth factors such as, for example, PDGF any mixtures of the proteins, in which case the composition of the mixture is likewise oriented to the required functional properties of the hydrogel.

Chosen enzyme inhibitors are, in particular, natural proteinogenic protease inhibitors from the class of TIMPs, and aprotinin, alpha-2-antiplasmin, alpha-2-macroglobulin, alpha-1-antichymotrypsin, soya bean trypsin inhibitor and alpha-1 protease inhibitor.

In the case of a protein-containing hydrogel which comprises SOD, catalase or a mixture of the two enzymes, it is possible to remove ROS selectively from the wound fluid. ROS are secreted in the inflammatory phase of wound healing by neutrophils and monocytes after a cellular stimulus. The enzyme SOD catalyses the dismutation reaction of reactive superoxide to the less toxic intermediates hydrogen peroxide and oxygen (equation 1). It plays the major role in cellular defence against the oxygen-mediated toxicity of ROS and in the regulation of the intracellular oxygen concentration (Fridovich, 1995, Annu. Rev. Biochem., 64, 97). The hydrogen peroxide formed by the SOD reaction is then converted by the redox enzyme catalase, which is ubiquitous in aerobic organisms, in a multistage catalytic cycle into the non-toxic molecules water and oxygen (equation 2) (Gouet et al., 1996, Nature Structural Biology, 3, 951). Apart from catalase, the enzymes glutathione peroxidase and myeloperoxidase are able to break down hydrogen peroxide.

$$2O_2^- + 2H^+ \rightarrow H_2O_2 + O_2 \quad (1)$$

$$H_2O_2 \rightarrow H_2O + \tfrac{1}{2}O_2 \quad (2)$$

Collagenase-containing ointments have been employed for some years to remove necrotic deposits covering wounds (Nano et al., 1996, in: Proteolysis in Wound Repair, Abatangelo, Donati and Vanscheidt (Eds.), Springer Verlag, Berlin, page 61) and J. Hansbrough & W. Hansbrough 1996, in: Proteolysis in Wound Repair, Abatangelo, Donati und Vanscheidt (Eds.), Springer Verlag, Berlin, page 97. This involves the enzyme collagenase and other proteases cleaving collagen molecules in the dead tissue and thus making it possible for fibroblasts to migrate in and thus heal the wound (Glyantsev et al., 1997, J. Wound Care, 6, 13). A hydrogel comprising collagenase contributes in a comparable manner to disintegrating the necrotic tissue.

The active enzymes are likewise removed when the hydrogel is removed and do not remain in the wound or in the wound fluid. This interaction includes according to the invention a conversion of the ROS as interfering factors into substances which no longer impede wound healing. The enzymes which are used for the interaction and are covalently bound into the hydrogel are thus only briefly introduced into the wound and are removed from the wound region again after they have performed their intended task (that is to say the abovementioned interactions have started). The selective removal or elimination of the toxic ROS, the proteolytic disintegration of dead tissue and the killing of microorganisms improves or initiates the healing process for chronic, that is to say wounds which are healing with difficulty or not at all.

The protease activity in a chronic wound is found to be distinctly increased (Weckroth et al., 1996, J. Invest. Dermatol., 106, 1119; Grinell & Zhu, 1996, J. Invest. Dermatol. 106, 335) compared with an acute wound. This contrasts with a distinct reduction in the amount of protease inhibitors (Grinell & Zhu, 1996, J. Invest. Dermatol. 106, 335). This imbalance results in proteolytic degradation of proliferation-promoting substances such as, for example, growth factors (Wlaschek et al., 1997, Brit. J. Dermatol., 137, 646). Enzymes such as, for example, SOD and catalase, which act to promote wound healing by their protective action, would thus undergo proteolytic degradation and become inactive. A protein-containing hydrogel into which such enzymes are covalently incorporated acts as a protective shield and is able to prevent attack by proteases, as has been shown with dissolved enzymes modified with polyethylene glycol (Beckman et al., 1988, J. Biol. Chem., 14, 6884; Inada et al., 1995, Tibtech, 13, 86).

It is thus possible within the scope of the present invention not only to generate a moist wound environment in order to improve the healing process for chronic wounds, but also to speed up further according to the invention the healing process by, for example, the abovementioned conversion processes.

Processes for producing the hydrogel according to the invention are explained in detail hereinafter.

In summary, an advantageous process for producing hydrogels according to the invention appears as follows:
a) anhydrous PEGs are reacted with diisocyanate in a solvent, where appropriate with the addition of a catalyst,
b) the solvent is removed from the resulting product of activated PEGs by filtration, washing or drying,
c) the activated PEGs are reacted in aqueous solution with proteins, the proteins being present in a buffer which is preferably chosen so that the proteins retain their biological activity,
d) where appropriate, purification steps and washes are carried out.

The hydrogel is preferably then dehydrated.

The hydrogel according to the invention is suitable particularly advantageously as wound dressing, in particular for deep and extensive chronic wounds, and burns.

The hydrogel furthermore shows advantageous properties on application to substrate materials which are, where appropriate, permeable to air and water vapor, such as bandages, compresses, plasters, sheets, films and the like.

The individual steps in the process are described in more detail below.

Production of Activated α,ω-diisocyanato-polyethylene Glycols

The experiments on the production of an activated polyethylene glycol are carried out as described below.

Polyethylene glycols of various molecular weights (6,000–35,000 g/mol) are converted by covalent linkage of aliphatic diisocyanates, to form urethane linkages, into α,ω-diisocyanato-polyethylene glycols. In order to avoid hydrolysis of the isocyanate groups employed, the PEG is dehydrated before the actual use. For this purpose, 1.0 mmol of PEG is dissolved in 60 ml of benzene and frozen in liquid nitrogen. The benzene/water azeotrope formed in this way is removed under high vacuum for 7 h. 1.0 mmol of the PEG dehydrated in this way is dissolved in 50 ml of abs. dichloromethane while maintaining an argon atmosphere. To this solution are added, for example, 10 mmol of hexamethylene diisocyanate and 1 ml of abs. pyridine and stirred at RT for 12 h. The reaction solution was worked up by reprecipitation twice in 800 ml of abs. petroleum ether 35/60. The crystalline product was filtered off on a Büchner funnel and washed with abs. petroleum ether 35/60 (2×100 ml). After drying under high vacuum for 8 h, the activated PEG is stored at −20° C. under an argon atmosphere.

It is possible to employ for activating the PEG according to the invention besides 1,6-hexamethylene diisocyanate also other aliphatic or aromatic diisocyanates, for example 1,12-dodecane diisocyanate, isophorone diisocyanate, methylcyclohexane 2,4- and/or 2,6-diisocyanate, dicyclohexylmethane 2,4'- and/or 4,4'-diisocyanate, also cyclobutane 1,3-diisocyanate, cyclohexane 1,3- and 1,4-diisocyanate, 2,4- and/or 2,6-hexahydrotolylene diisocyanate, hexahydro-1,3- and/or 1,4-phenylene diisocyanate, and 1,3- and 1,4-phenylene diisocyanate, 2,4- and 2,6-tolylene diisocyanate, diphenylmethane 2,4'- and/or 4,4'-diisocyanate and naphthylene 1,5-diisocyanate.

Production of Protein-containing Hydrogels

It has been found, surprisingly, that the novel reaction of the α,ωdiisocyanato-polyethylene glycols with proteins to form protein-containing hydrogels is associated with considerably shorter gel times by comparison with 4-nitrophenyl chloroformate activation.

FIG. 1 is a graphical depiction of the dependence of the gel time on the molecular weight of the α,ω-diisocyanato-polyethylene glycols employed and the pH of the reaction solution. In this, the molecular weight of the PEG employed in gram/mole is depicted on the x axis, and the gel time in seconds is depicted on the y axis. Furthermore, three 0.1 M borate buffer solutions of different pH values are depicted (○=pH 9.5, □=pH 9.0, Δ=pH 8.5).

Figure 2:
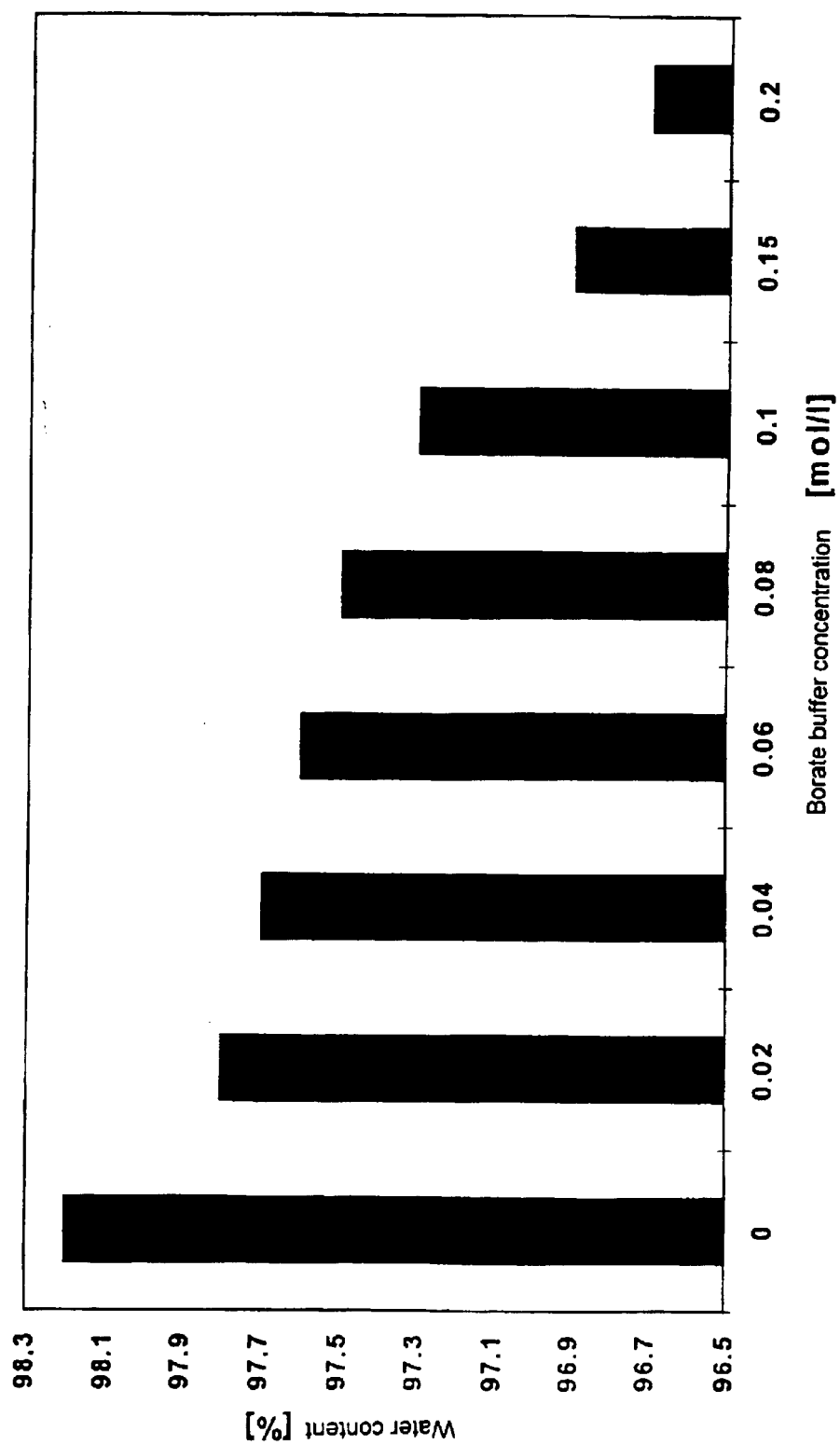

FIG. 2 is a graphical depiction of the dependence of the maximal amount of water which can be absorbed on the ionic strength of the incubation solution. The water content as a percentage of the total weight of the hydrogels is depicted on the x axis, while the ionic strength of the incubation solution is shown in the form of the borate concentration, increasing from 0–0.2 mol per liter, on the y axis. The depicted experiment took place with hydrogels of the composition 100 mg of $PEG_{15000}$ and 35 mg of BSA.

As described above, it was not previously possible to immobilize proteins, other than albuminoid ones, isolated, in three-dimensional form within a hydrogel matrix. If there was observable gel formation with other proteins or enzymes, they dissolved within a few minutes (see U.S. Pat. No. 5,733,563) and it was possible to achieve only an immobilization as a ternary system consisting of PEG/BSA/enzyme (Fortier et al. 1996. Enz. Microbiol.Technol. 18, 482).

It has further emerged, surprisingly, that the described form of PEG activation via diisocyanates permits immobilization of proteins and enzymes other than albuminoid ones, such as bovine and yeast superoxide dismutase (SOD). For this purpose, 44 mg of superoxide dismutase are dissolved in 2 ml of 0.1 M borate buffer and mixed with 150 mg PEG of various molecular weights. After crosslinking the SOD hydrogels are washed in analogy to BSA hydrogels by incubation in physiological borate buffer, and the washing solution is investigated for uncrosslinked PEG and enzyme. It is found thereby that, under certain conditions, gel formation takes place to result in a stable SOD hydrogel. An essential factor in this connection proves to be the molecular weight and thus the chain length of the polyethylene glycols employed. Gel formation is possible only with difficulty above a molecular weight of $PEG_{20000}$.

In order to estimate the retention of enzymatic activity, samples of the prepared SOD hydrogels are investigated for their activity with the aid of NBT detection (Auclair and Voisin, 1985, in: CRC Handbook of Methods for Oxygen Radical Research, CRC Press Inc., Boca Raton). Since this test is suitable only for the quantitative determination of dissolved SOD, it is possible therewith to obtain only qualitative information about the presence of immobilized SOD activity. However, the results obtained suggest that the immobilization within the gel matrix appears to have no significant effect on the activity of the enzyme. Even after storage at various temperatures (4° C., 25° C., 37° C.) for several weeks, followed by dehydration under high vacuum and reswelling in incubation solution the enzymic activity present can be observed to be unchanged.

Based on these results, the experiments were extended to other enzymes. This entails testing the crosslinking possibility for the following enzymes:

bovine catalase chicken egg white lysozyme and collagenase from *Achromobacter iophagus*.

It is possible with all the said enzymes to obtain a stable hydrogel, the limiting factor being the chain length of the PEG molecule employed.

TABLE 1

Crosslinking possibilities for various proteins and enzymes with α,ω-diisocyanato-PEG.
All the experiments took place in 2 ml of 0.1 M borate buffer (pH 9.0) with 150 to 300 mg of PEG and 35 to 100 mg of protein/enzyme.

|  | $PEG_{15000}$ | $PEG_{10000}$ | $PEG_{6000}$ |
| --- | --- | --- | --- |
| BSA | x | x | x |
| SOD | x | x | x |
| catalase | x | x | x |
| collagenase | x | x |  |
| lysozyme | x | x | x |
| phosphatase |  | x | x |
| trypsin |  | x | x |
| SOD/catalase | x | x | x |

Method for Washing the Protein-containing Hydrogels

After the crosslinking is complete, the hydrogels are incubated in 15 ml of physiological borate buffer (0.1 M $H_3BO_3$, 0.1 M $MgCl_2$, 0.1 M $CaCl_2$, 0.15 M NaCl; pH 7.0) at RT. The incubation solution is changed every 12 hours, and the resulting supernatant is investigated for washed-out protein and PEG. The resulting amounts of protein were evaluated by means of BCA and micro-BCA detection (Brown, Jarvis and Hyland, 1989, Anal. Biochem., 180, 136) and the eluted amounts of PEG were determined with the aid of iodine detection (Sims and Snape, 1980, Anal. Biochem., 107, 60).

The washing is complete when neither protein nor PEG is detectable in the washing solution (incubation between 48–72 h). The hydrogels are then stored at RT either in dehydrated (see the method for dehydrating protein-containing hydrogels) or in swollen form.

Method for Dehydrating the Protein-containing Hydrogels

After completion of the washing process, the gels are dehydrated under high vacuum to constant weight and incubated anew in buffer solutions in order for us to investigate the dependence of the water absorption on various factors such as pH and ionic strength of the hydrogels. The swelling of the gels is followed until the maximum water absorption capacity is reached, by regularly determining the weight, changing the incubation solution every 12 h. The swelling factor (SF) [equation 3] and the maximum water content (EWC) [equation 4] are described by two mathematical relations used for determining the swelling characteristics of polyvinyl alcohol hydrogels (Urushisaki et al., 1990, Int. J. Pharm., 58, 135):

$$\text{Swelling factor } (SF) = (W_s - W_d)/W_d \quad (3)$$

In this, $W_s$ corresponds to the maximum swelling weight achievable and $W_d$ corresponds to the dry weight of the hydrogels. This dry weight is determined after completion of the investigations by drying the gels at 70° C. over a period of 24 h. The water content as a percentage of the total weight of the hydrogels can be determined from the data obtained:

$$EWC = (\text{weight of water/weight of swollen hydrogel}) \times 100 \quad (4)$$

Experiments concerning the swelling characteristics at different pH values and ionic strengths of the incubation solutions have shown that there is a direct connection between these parameters and the swelling capacity of the hydrogels. If, for example, an increase in the ionic strength of the incubation solution causes a decrease in the water absorption capacity, the contrary effect can be observed on changing the pH of the incubation solution. In this case, an increase in the pH leads to an Increase In the water absorption capacity.

The effect of the molecular weight of the polyethylene glycols employed on the swelling characteristics of the resulting hydrogels is shown in detail in Table 1.

TABLE 2

Evaluation of the swelling parameters (swelling factor SF and water content EWC) of various hydrogels of the following composition: 100 mg of α,ω-diisocyanato-$PEG_x$ and 35 mg of BSA in 2 ml 0.1 M borate buffer solution (pH 9.0).
The following swelling parameters were determined after incubation in physiological borate buffer (0.1 M $H_3BO_3$, 1 M $MgCl_2$, 1 M $CaCl_2$, 0.15 M NaCl; pH 7.0) at RT for 72 h and drying at 70° C. for 24 h.

| m PEG [g/mol] | SF X | EWC [%] |
|---|---|---|
| 6,000 | 29.3 | 96.7 |
| 10,000 | 35.9 | 97.3 |
| 15,000 | 43.4 | 97.7 |
| 20,000 | 47.2 | 97.9 |
| 35,000 | 63.4 | 98.5 |

It should be noted in this connection that the water absorption capacity increases continuously in the direction of higher PEG molecular weights employed. A repetition of the experiment after drying the hydrogels (dehydration under high vacuum to a constant weight) shows irreversibility in relation to the maximum water absorption capacity. In fact, the water contents after renewed swelling following a drying step are 60–70% of the water contents achievable before drying.

Concerning the oxygen permeability of the present hydrogels, it can be assumed that, from a water content >94% onwards, the oxygen diffusion within the hydrogels will correspond to that of an aqueous solution (Corkhill et al. 1990, Crit. Rev. Biocompatibility., 5, 363).

Method for SOD Activity Determination

The Biotech SOD-525 assay (OXIS International S.A., France) was employed for measuring the activity of the various SOD enzymes. This assay is based on the increase caused by SOD in the rate constant for the autoxidation reaction of the catechol 5,6,6a,11b-tetrahydro-3,9,10-trihydroxybenzo[c]fluorene (BXT-01050) in aqueous alkaline solution (Nebot et al., 1993, Analytical Biochemistry, 214, 442). This autoxidation reaction produces a chromophore with a maximum absorption at 525 nm. The assay is carried out in an air-saturated buffer containing 50 mM 2-amino-2-methyl-1,3-propanediol, 0.1 mM diethylenetriaminepentaacetic acid and 3 mM boric acid, pH 8.8, at 37° C. Kinetics are measured at 525 nm within one minute after addition of BXT-01050. The SOD activity is determined by the ratio of the rate constant for the autoxidation reaction $V_s/V_c$, measured in the presence ($V_s$) and in the absence ($V_c$) of the sample. One SOD unit (U-525) is defined as the activity which doubles the background of the autoxidation reaction, that is to say $V_s/V_c=2$.

Method for Catalase Activity Determination

Catalase (EC 1.11.1.6, Boehringer Mannheim) catalyses the cleavage of hydrogen peroxide ($H_2O_2$) into oxygen and water. Determination of the activity of the dissolved enzyme takes place using a modification of the spectrophotometric assay of R. F. Beers and I. W. Sizers (J. Biol. Chem. 195, 133 (1952)). The decrease in extinction at 240 nm correlates in this case with the decrease in hydrogen peroxide due to catalase activity in the reaction mixture.

3 ml of phosphate buffer (50 mM, pH 7.0) (reference position) or 3 ml of a phosphate buffer (0.05 mM, pH 7) mixed with $H_2O_2$ (sample), each with 0.05 ml of the catalase-containing sample, are placed in a quartz cuvette. The hydrogen peroxide concentration in the $H_2O_2$-containing buffer is checked by measuring the extinction at 240 nm, the absorption thereof being 0.500+/−0.01. After mixing the components in the quartz cuvettes (path length 10 mm), the reaction is observed until the extinction reaches a value of 0.450. The time then taken for the extinction to diminish to 0.400 is then measured using a stop clock. The enzyme concentration in the cuvette is adjusted so that the time needed for this is 20 s +/−2 s The volume-based activity is calculated by the following formula:

volume-based activity [U/ml]=(17×13)/measured times [s]×0.05 total activity in the sample [U]=vol. act. [U/ml]×dilution×sample volume [ml]

One unit is defined as the enzymic activity which disproportionates 1 μmol of hydrogen peroxide per minute under the chosen assay conditions (25° C., pH 7.0).

Method for Collagenase Activity Determination

Collagenase (EC 3.4.24.3, Boehringer Mannheim) catalyses the hydrolytic cleavage of N-(3[2-furyl]acryolyl)-Leu-Gly-Pro-Ala (FALGPA) (Sigma Chemical Steinheim) at the peptide linkage between the amino acids leucine and glycine in the substrate. The determination of the activity of the dissolved enzyme takes place with a modification of the spectrophotometric assay of H. E. van Wart and D. R. Steinbrink (Anal. Biochem. 113, 356 (1981)). The increase in extinction at 345 nm in this case correlates with the release of coloured N-(3-[2-furyl]acryloyl)-Leu from the substrate due to collagenase activity in the reaction mixture.

In a quartz cuvette (path length 10 mm, Hellma Jena) 2.9 ml of buffer solution (50 mM tricine, 10 mM calcium chloride, 400 mM sodium chloride, pH 7.5) are mixed with 0.1 ml of the collagenase-containing (2 units/ml) sample (sample position) or with 0.1 ml of distilled water (reference position). After mixing the components in the quartz cuvettes and adjusting the temperature to 25° C., the resulting extinction difference at 345 nm is checked over a period of five minutes. The volume-based activity of the sample is calculated by the following formula:

volume-based activity of the sample [U/ml]=DE nm/min sample— DE nm/min reference position/(0.53)×(mg enzyme/ml reaction mix)

DE=extinction difference

Total activity in the sample [U]=vol.act. [U/ml]×dilution×sample volume [ml]

One unit is defined as the enzymic activity which hydrolyses 1.0 mmol of FALGPA per minute under the chosen assay conditions (25° C., pH 7.5).

Method for Trypsin Activity Determination

Trypsin (EC 3.4.21.4, Sigma Chemical Steinheim) catalyses the cleavage of peptide linkages at the C-terminal end of the amino acids arginine and lysine. The determination of the activity of the dissolved enzyme takes place with a modification of the spectrophotometric assay of Hummel (Can. J. Biochem. Physiol. 37, 1393 (1959)). The increase in extinction at 257 nm correlates with the release of p-toluenesulphonyl-1-arginine from p-toluenesulphonyl-1-arginine methyl ester (Sigma Chemical Steinheim).

2.6 ml of buffer solution (0.65 M tris(hydroxymethyl) aminomethane, 11 mM calcium chloride dehydrate, pH 8.1) and 0.3 ml of substrate solution (10 mM p-toluenesulphonyl-1-arginine methyl ester) are placed in a quartz cuvette (path length 10 mm, Hellma Jena), and 0.1 ml of enzyme solution (0.5 U in 1 ml of 0.001 N hydrochloric acid) is added. After mixing in the quartz cuvette and adjusting the temperature to 25° C., the increase in extinction is determined with distilled water as reference over a period of 5 minutes, a constant value per minute being found. The volume-based activity of the sample is calculated by the following formula:

volume-based activity of the sample [U/ml]=DE nm/min sample× sample volume/(0.54)×(mg enzyme/ml reaction mix)

DE=extinction difference

Total activity of the sample [U]=vol.act. [U/ml]×dilution×sample volume [ml]

One unit is defined as the enzymic activity which brings about the formation of 1 mmol of p-toluenesulphonyl-1-arginine per minute under the chosen assay conditions (25° C., pH 7.5).

Method for Elastase Activity Determination

Elastase (EC 3.4.21.36, Sigma Chemical Steinheim) catalyses the cleavage of, for example, elastin to amino acids and peptides. Determination of the activity of the dissolved enzyme takes place with a modification of the spectrophotometric assay of Sacher et al. (Proc. Soc. Exp. Biol. Med. 90, 1955 (1955)). The increase in extinction at 590 nm correlates with the hydrolytic release of orcein from elastin-orcein (Sigma Chemical Steinheim).

20 mg of elastin-orcein are weighed into an Erlenmeyer flask, and 1.5 ml of tris(hydroxymethyl)-aminomethane hydrochloride (197 mM, pH 8.8) are added and equilibrated at 37° C. After addition of 0.5 ml of enzyme solution, the flask is stoppered and stored at 37° C. After addition of 2 ml of phosphate buffer solution (500 mM, pH 6.0) the reaction Is stopped after 20 minutes. The mixture is filtered and the flask is rinsed with 1 ml of distilled water. The extinction of 3 ml of sample solution in a quartz cuvette (path length 10 mm, Hellma Jena) is determined at 590 nm, with the reference position comprising 3 ml (2.0 ml of tris (hydroxymethyl)aminomethane hydrochloride (197 mM, pH 8.8), 2.0 ml of phosphate buffer solution (500 mM, pH 6.0) and 1.0 ml of distilled water). The volume-based activity of the sample is calculated by the following formula:

volume-based activity of the sample [U/ml]=$E_{590}$ ×19.45–0.1185= mg of elastin-orcein cleaved/(mg enzyme/0.5 ml reaction mix)

total activity of the sample [U]=vol.act. [U/mil]×dilution×sample volume [ml]

One unit is defined as the enzymic activity which cleaves 1 mg of elastin within 20 min under the chosen assay conditions (37° C., pH 8.8).

Further examples which follow are intended to show particularly advantageous embodiments of the invention without intending unnecessarily to restrict the invention thereby.

EXAMPLE 1

Production of Hydrogels with Serum Albumin

The hydrogels are synthesized by covalent crosslinking of α,ω-activated PEG with bovine serum albumin. Various amounts (1–20% m/V) of activated PEG are added to a 2% strength (m/V) protein solution in 0.1 M borate buffer (pH 6.5–9.0) and stirred until the onset of the gel point. The hydrogel which is formed is then stored at RT for 12 h to achieve complete crosslinking. Uncrosslinked PEG and protein are removed by incubating the hydrogel in 15 ml of physiological borate buffer (0.1 M $H_3BO_3$, 1M $MgCl_2$, 1 M $CaCl_2$, 0.15 M NaCl: pH 7.0) for 48 h, changing the washing solutions several times. The amounts of protein eluted thereby are evaluated with the aid of the BCA and micro-BCA detection (Brown, Jarvis and Hyland, 1989, Anal. Biochem., 180, 136) and the eluted amounts of PEG are evaluated by means of the iodine detection (Sims and Snape, 1980, Anal. Biochem.,107, 60).

The crosslinking reaction takes place analogously in 0.05 M sodium bicarbonate buffer with pH values 8.5, 9.0 and 9.3 and in a 0.1 M sodium veronal buffer at pH 9.0. The hydrogels produced in sodium phosphate buffer can be kept stable by changing to physiological borate buffer.

The following depiction shows the crosslinking of $PEG_{35000}$ with bovine serum albumin (BSA) diagrammatically.

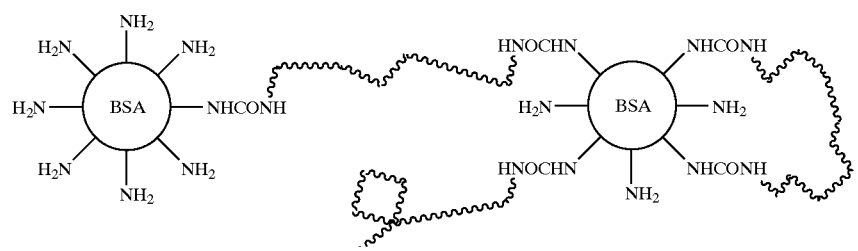

-continued

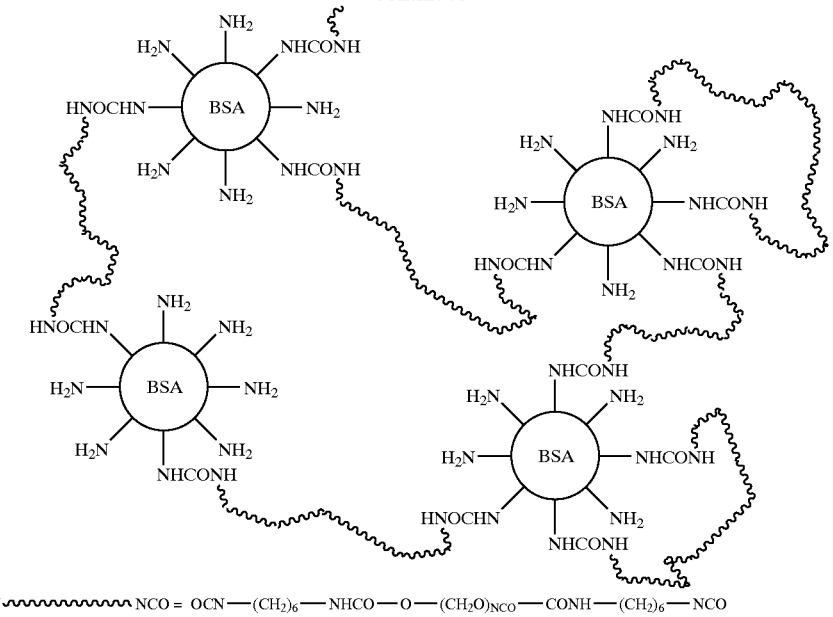

N∼∼∼∼∼NCO = OCN—(CH$_2$)$_6$—NHCO—O—(CH$_2$O)$_{NCO}$—CONH—(CH$_2$)$_6$—NCO

EXAMPLE 2

Production of Hydrogels with Superoxide Dismutase

The ubiquitous enzyme SOD occurs in dimeric or tetrameric form. The various enzymes with molecular weights from 32,000 to 56,000 Da have metal ions such as copper and zinc (Cu—Zn—SOD), manganese (Mn—SOD) or iron (Fe—SOD) as cofactors in the catalytic center.

The hydrogels are synthesized by covalent crosslinking of α,ω-activated PEG with bovine and yeast superoxide dismutase. Various amounts (6–25% m/V) of activated PEG are added to a 2% strength (m/V) protein solution in 0.1 M borate buffer (pH 9.0) and stirred until the onset of the gel point. Greenish transparent gels are obtained. The hydrogels are then stored at RT for 12 h in order to achieve complete crosslinking. Uncrosslinked PEG and protein are removed by incubating the hydrogels in 15 ml of physiological borate buffer (0.1 M H$_3$BO$_3$, 0.1 M MgCl$_2$, 0.1 M CaCl$_2$, 0.15 M NaCl; pH 7.0) for 48 h changing the washing solutions several times. Gel formation was observed for the PEG: PEG$_{20000}$, PEG$_{15000}$, PEG$_{10000}$ and PEG$_{6000}$.

EXAMPLE 3

Production of Hydrogels with Catalase

The most widespread form of catalase is a homotetramer (235.000 Da, bovine liver) with a porphyrin group with one iron atom per subunit.

The hydrogels are synthesized by covalent crosslinking of α,ω-activated PEG with catalase from bovine liver. 7.5% (m/V) activated PEG$_{10000}$ or 15% (m/V) activated PEG$_{6000}$ are added to a 2.5% strength (m/V) protein solution in 0.1 M borate buffer (pH 9.0) and stirred until the onset of the gel point. Brownish transparent gels are obtained.

The hydrogels are then stored at RT for 12 h in order to achieve complete crosslinking. Uncrosslinked PEG and protein are removed by incubating the hydrogels in 15 ml of physiological borate buffer (0.1 M H$_3$BO$_3$, 0.1 M MgCl$_2$, 0.1 M CaCl$_2$, 0.15 M NaCl; pH 7.0) for 48 h changing the washing solutions several times.

EXAMPLE 4

Production of Hydrogels with Superoxide Dismutase and Catalase

The hydrogels are synthesized by covalent crosslinking of α,ω-activated PEG with yeast superoxide dismutase and bovine liver catalase. 0.8–0.15% (m/V) catalase and 5% (m/V) activated PEG are added to a 2.4% (m/V) superoxide dismutase solution in 0.1 M borate buffer (pH 9.0) and stirred until the onset of the gel point. Greenish/brownish transparent gels are obtained.

The hydrogels are then stored at RT for 12 h to achieve complete crosslinking. Uncrosslinked PEG and protein are removed by incubating the hydrogels in 15 ml of physiological borate buffer (0.1 M H$_3$BO$_3$, 0.1 M MgCl$_2$, 0.1 M CaCl$_2$, 0.15 M NaCl; pH 7.0) for 48 h, changing the washing solutions several times. Gel formation was observed for PEG$_{10000}$ and PEG$_{6000}$.

EXAMPLE 5

Production of hydrogels with Collagenase

The hydrogels are synthesized by covalent linking of α,ωactivated PEG with collagenase from Achromobacter iophagus. 7.5–15% (m/V) activated PEG15000 or activated PEG10000 are added to a 5% strength (m/V) protein solution in 0.1 M borate buffer (pH 9.0) and stirred until the onset of the gel point. Reddish/brownish transparent gels are obtained.

The hydrogels are then stored at RT for 12 h to achieve complete crosslinking. Uncrosslinked PEG and protein are removed by incubating the hydrogels in 15 ml of physiological borate buffer (0.1 M H$_3$BO$_3$, 0.1 M MgCl$_2$, 0.1 M CaCl$_2$, 0.15 M NaCl; pH 7.0) for 48 h, changing the washing solutions several times.

EXAMPLE 6

Production of Hydrogels with Lysozyme

The hydrogels are synthesized by covalent crosslinking of α,ωactivated PEG with lysozyme from chicken egg white.

7.5–15% (m/V) activated PEG are added to a 2.5–5% strength (m/V) protein solution in 0.1 M borate buffer (pH 9.0) and stirred until the onset of the gel point. Gels with a milky cloudiness are obtained. The hydrogels are then stored at RT for 12 h to achieve complete crosslinking. Uncrosslinked PEG and protein are removed by incubating the hydrogel in 15 ml of physiological borate buffer (0.1 M $H_3BO_3$, 0.1 M $MgCl_2$, 0.1 M $CaCl_2$, 0.15 M NaCl; pH 7.0) for 48 h, changing the washing solutions several times. Gel formation could be observed for the following PEG: $PEG_{35000}$, $PEG_{20000}$, $PEG_{15000}$, $PEG_{10000}$ and $PEG_{6000}$.

EXAMPLE 7

Production of Hydrogels with Trypsin

The hydrogels were synthesized by covalent crosslinking of α,ω-activated PEG with bovine trypsin. 7.5–15% (m/V) activated PEG were added to a 2.5–5% strength (m/V) protein solution in 0.1 M borate buffer (pH 9.0) and stirred until the onset of the gel point. Gels with a milky cloudiness were obtained. The hydrogels were then stored at RT for 12 h to achieve complete crosslinking. Uncrosslinked PEG and protein were removed by incubating the hydrogel in 15 ml of physiological borate buffer (0.1 M $H_3BO_3$, 0.1 M $MgCl_2$, 0.1 M $CaCl_2$, 0.15 M NaCl; pH 7.0) for 48 h, changing the washing solutions several times. Gel formation could be observed for the following PEG: $PEG_{10000}$ and $PEG_{6000}$.

EXAMPLE 8

Production of Hydrogels with Phosphatase

The hydrogels were synthesized by covalent crosslinking of α,ωactivated PEG with wheatgerm phosphatase. 10–15% (m/V) activated PEG were added to a 2.5% strength (m/V) protein solution in 0.1 M borate buffer (pH 9.0) and stirred until onset of the gel point. Brownsih gels were obtained. The hydrogels were then stored at RT for 12 h to achieve complete crosslinking. Uncrosslinked PEG and protein were removed by incubating the hydrogel in 15 ml of physiological borate buffer (0.1 M $H_3BO_3$, 0.1 M $MgCl_2$, 0.1 M $CaCl_2$, 0.15 M NaCl; pH 7.0) for 48 h, changing the washing solutions several times. Gel formation could be observed for the following PEG: $PEG_{10000}$ and $PEG_{6000}$.

What is claimed is:

1. A protein-containing hydrogel comprising a polyethylene glycol (PEG) matrix to which is bound one or more catalytically active polypeptides or proteins, wherein,
   (a) the matrix comprises an activated diisocyanato-PEG polymer further comprising unblocked urea groups;
   (b) the one or more catalytically active polypeptides or proteins possessing free radical scavenging activity; and
   (c) wherein the one or more catalytically active polypeptides or proteins are directly bound to the diisocyanato-PEG matrix via the unblocked urea groups.

2. The hydrogel of claim 1, wherein the one or more catalytically active polypeptides or proteins is selected from the group consisting of catalase, superoxide dismutase, lactoperoxidase, glutathione peroxidase, myeloperoxidase, thyroid peroxidase, or a mixture thereof.

3. The hydrogel of claim 1, wherein the one or more catalytically active polypeptides or proteins comprise catalase.

4. The hydrogel of claim 1, wherein the one or more catalytically active polypeptides or proteins comprise superoxide dismutase.

5. The hydrogel of claim 2, further comprising one or more metal-porphyrin complexes, and further wherein at least one of the metals is selected from the group consisting of iron, copper, magnesium and manganese.

6. The hydrogel of claim 5, wherein the metal moiety of the metal-porphyrin complexes is selected from the group consisting of iron, copper, magnesium and manganese.

7. The hydrogel of claim 2, wherein the PEG has a molecular weight of from 8,000 to 18,000 g/mol.

8. The hydrogel according to claim 1, wherein the PEGs are activated by aliphatic, aromatic or araliphatic diisocyanates.

9. The hydrogel according to claim 5, wherein the diisocyanate is 1,6 hexamethylene diisocyanate.

10. The hydrogel of claim 1, further comprising one or more catalytically active polypeptides or proteins selected from the group consisting of proteases, metalloproteases and hydrolases.

11. The hydrogel of claim 10, further comprising one or more catalytically active polypeptides or proteins selected from the group consisting of trypsin, collagenase, lysozyme, elastase, and phosphatase.

12. A process for preparing the protein-containing hydrogel of claim 1, the process comprising the steps:
   (a) preparing the activated diisocyanato-PEG polymer having unblocked urea groups by reacting PEG with a diisocyanate in a solvent, wherein the reacting optionally takes place in the presence of a catalyst;
   (b) removing the solvent from the activated diisocyanato-PEG polymer;
   (c) contacting the activated diisocyanato-PEG polymer with the one or more catalytically active polypeptides or proteins under conditions that effectively permit the one or more polypeptides and proteins to covalently attach to the activated diisocyanato-PEG polymer by reacting with the unblocked urea groups.

13. The process of claim 12, wherein the diisocyanate is either an aliphatic, aromatic or araliphatic diisocyanate.

14. The process of claim 12 wherein the diisocyanate is selected from the group consisting of 1,6-hexamethylene diisocyanate, 1,12-dodecane diisocyanate, isophorone diisocyanate, methylcyclohexane 2,4- and/or 2,6-diisocyanate, dicyclohexylmethane 2,4'- and/or 4,4'-diisocyanate, cyclobutane 1,3-diisocyanate, cyclohexane 1,3- and 1,4-diisocyanate, 2,4- and/or 2,6-hexahydrotolylene diisocyanate, hexahydro-1,3- and/or 1,4-phenylene diisocyanate, and 1,3- and 1,4-phenylene diisocyanate, 2,4- and 2,6-tolylene diisocyanate, diphenylmethane 2,4'- and/or 4,4'-diisocyanate and naphthylene 1,5 diisocyanate.

15. The process of claim 12 wherein the diisocyanate is 1,6-hexamethylene diisocyanate.

16. The process of claim 12 wherein the PEG is of a molecular weight between 6,000 g/mol to 35,000 g/mol.

17. The process of claim 12 wherein the PEG is of a molecular weight between 8,000 g/mol to 18,000 g/mol.

18. The process of claim 12 wherein the PEG is of a molecular weight between 10,000 g/mol to 15,000 g/mol.

* * * * *

UNITED STATES PATENT AND TRADEMARK OFFICE
CERTIFICATE OF CORRECTION

PATENT NO. : 6,773,703 B1
DATED : August 10, 2004
INVENTOR(S) : Ettner et al.

It is certified that error appears in the above-identified patent and that said Letters Patent is hereby corrected as shown below:

Column 1,
Line 1, "since lime" should read -- since time --
Line 52, "of research, These" should read -- of research. These --

Column 3,
Line 8, "(PEGS)" should read -- (PEGs) --

Column 5,
Line 10, "R4" should read -- $R_4$ --

Column 6,
Lines 8, 25 and 43, "R4" should read -- $R_4$ --
Line 52, "Independently of" should read -- independently of --

Column 7,
Lines 30 and 55, "R4" should read -- $R_4$ --

Column 8,
Line 15, "$R_2$. $R_3$, R4" should read -- $R_2$, $R_3$, $R_4$" --

Column 13,
Line 7, "an Increase In the" should read -- an increase in the --

Column 15,
Line 50, "Is stopped" should read -- is stopped --

Column 16,
Line 13, "[U/mil]" should read -- [U/ml] --

Column 18,
Lines 51 and 67, "α,ωactivated" should read -- α,ω-activated --
Line 52, "PEG15000" should read -- $PEG_{15000}$ --
Line 53, "PEG10000" should read -- $PEG_{10000}$ --

UNITED STATES PATENT AND TRADEMARK OFFICE
CERTIFICATE OF CORRECTION

PATENT NO. : 6,773,703 B1
DATED : August 10, 2004
INVENTOR(S) : Ettner et al.

It is certified that error appears in the above-identified patent and that said Letters Patent is hereby corrected as shown below:

Column 19,
Line 34, "$\alpha,\omega$activated" should read -- $\alpha,\omega$-activated --

Signed and Sealed this

Twenty-second Day of February, 2005

JON W. DUDAS
*Director of the United States Patent and Trademark Office*